United States Patent
Schulte et al.

(10) Patent No.: US 10,232,015 B2
(45) Date of Patent: Mar. 19, 2019

(54) SUGAR COMPOSITIONS FOR TREATING HEMOPHILIA A AND/OR VON WILLEBRAND DISEASE

(71) Applicant: CSL Behring GmbH, Marburg (DE)

(72) Inventors: Stefan Schulte, Marburg (DE); Rolf Spirig, Bern (CH); Sabine Zollner, Muri (CH); Michael Moses, Graevenwiesbach (DE); Wilfried Wormsbaecher, Kirchhain (DE); Hans-Arnold Stoehr, Wetter (DE)

(73) Assignee: CSL BEHRING GMBH, Marburg (DE)

( * ) Notice: Subject to any disclaimer, the term of this patent is extended or adjusted under 35 U.S.C. 154(b) by 0 days.

(21) Appl. No.: 15/622,447

(22) Filed: Jun. 14, 2017

(65) Prior Publication Data
US 2017/0274045 A1   Sep. 28, 2017

Related U.S. Application Data

(63) Continuation of application No. 14/399,326, filed as application No. PCT/EP2013/055474 on Mar. 15, 2013, now Pat. No. 9,707,269.

(30) Foreign Application Priority Data

May 8, 2012 (EP) ..................... 12167178

(51) Int. Cl.
*A61K 38/17* (2006.01)
*A61K 31/7016* (2006.01)
*A61K 31/7008* (2006.01)
*A61K 31/70* (2006.01)
*A61K 31/7004* (2006.01)

(52) U.S. Cl.
CPC .......... *A61K 38/1709* (2013.01); *A61K 31/70* (2013.01); *A61K 31/7004* (2013.01); *A61K 31/7008* (2013.01); *A61K 31/7016* (2013.01)

(58) Field of Classification Search
None
See application file for complete search history.

(56) References Cited

U.S. PATENT DOCUMENTS

2008/0038232 A1   2/2008   Shaaltiel et al.
2011/0110921 A1   5/2011   Dockal et al.

FOREIGN PATENT DOCUMENTS

| WO | WO 2005/117912 A1 | 12/2005 |
| WO | WO 2010/003687 A1 | 1/2010 |
| WO | WO 2010/020423 A2 | 2/2010 |
| WO | WO 2010/020423 A3 | 2/2010 |
| WO | WO 2011/017414 A2 | 2/2011 |

OTHER PUBLICATIONS

A. N. Zelensky et al., "The C-type lectin-like domain superfamily", FEBS Journal, vol. 272, pp. 6179-6217 (2005).
C.M. Millar et al., "Oligosaccharide structures of von Willebrand factor and their potential role in von Willebrand disease", Blood Reviews, vol. 20, pp. 83-92 (2006).
CSL Behring GmbH, "Humate-P® Prescribing Information", 2014, pp. 1-8.
Ellies et al., "Sialyltransferase ST3Gal-IV operates as a dominant modifier of hemostasis by concealing asialoglycoprotein receptor ligands" PNAS, 2002, pp. 10042-10047.
International Search Report from the European Patent Office for International Application No. PCT/EP2013/055474 dated Aug. 2, 2013.
K. Canis et al., "The plasma von Willebrand factor O-glycome comprises a surprising variety of structures including ABH antigens and disialosyl motifs". Journal of Thrombosis and Haemostasis, vol. 8, pp. 137-145 (2009).
K. Fijnvandraat et al., "Inter-individual variation in half-life of infused recombinant factor VIII is related to pre-infusion von Willebrand factor antigen levels", British Journal of Haematology, vol. 91, pp. 474-476 (1995).
Matsui, T. et al., "Comparative study of blood group-recognizing lectins toward ABO blood group antigens on neoglycoproteins, glycoproteins and comples-type oligosaccharides," Biochimica et Biophysica Acta 1525 (2011), pp. 50-57.
P.J. Lenting et al., "Clearance mechanisms of von Willebrand factor and factor VIII", Journal of Thrombosis and Haemostasis, vol. 5, pp. 1353-1360 (2007).
P.V. Jenkins et al., "ABO blood group determines plasma von Willebrand factor levels: a biologic function after all?", Transfusion, vol. 46, pp. 1836-1844 (2006).
Partial European Search Report from the European Patent Office for corresponding European Application No. EP 12 16 7178 dated Jul. 26, 2012.
PCT Preliminary Report on Patentability for PCT/EP2013/055474, dated Nov. 20, 2014 (12 pages).
Pendu et al., "Mouse models of von Willebrand disease", Journal of Thrombosis and Haemostasis, 2009, pp. 61-64.
S. Lethagen et al., "von Willebrand factor/factor VIII concentrate (Haemate® P) dosing based on pharmacokinetics: a prospective multicenter trial in elective surgery", Journal of Thrombosis and Haemostasis, vol. 5, pp. 1420-1430 (2007).
S.F. De Meyer et al., "von Willebrand factor to the rescue", Blood, vol. 113, pp. 5049-5057 (2090).
The Canadian Blood Service, "FVIII/vWF Products Comparison Table", obtained from https://www.blood.ca/sites/default/files/FVIII_vWF-Products-Comparison-Table.pdf on May 21, 2016; published Apr. 11, 2008.
Turecek et al., "In Vivo Characterization of Recombinant von Willebrand Factor in Dogs With von Willebrand Disease", Blood, 1997: pp. 3555-3567.

(Continued)

*Primary Examiner* — Lianko G Garyu
(74) *Attorney, Agent, or Firm* — Finnegan, Henderson, Farabow, Garrett & Dunner, L.L.P.

(57) ABSTRACT

The invention relates to compositions comprising an isolated sugar for use in the treatment of von Willebrand disease and/or hemophilia A, wherein the sugar is an accessible sugar residue derived from ABO(H) blood group antigen.

20 Claims, 19 Drawing Sheets

(56) References Cited

OTHER PUBLICATIONS

Van Schooten, C. et al., "Variations in glycosylation of von Willebrand factor with O-linked sialylated T antigen are associated with its plasma levels," *Hemostatis, Thrombosis, and Vascular Biology*, vol. 109, No. 6 (Mar. 15, 2007), pp. 2430-2437.
Written Opinion from the European Patent Office for International Application No. PCT/EP2013/055474 dated Aug. 2, 2013.
Yet et al., The Covalent Structure of Individual N-Linked Glycopeptides from Ovomucoid and Asialofetuin, The Journal of Biological Chemistry, 1988, pp. 111-117.

Figure 9, continued:
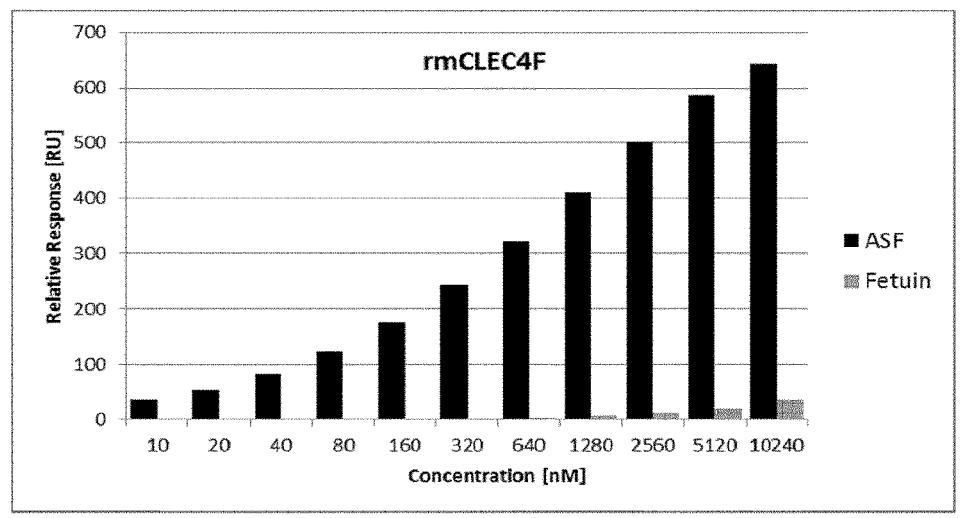
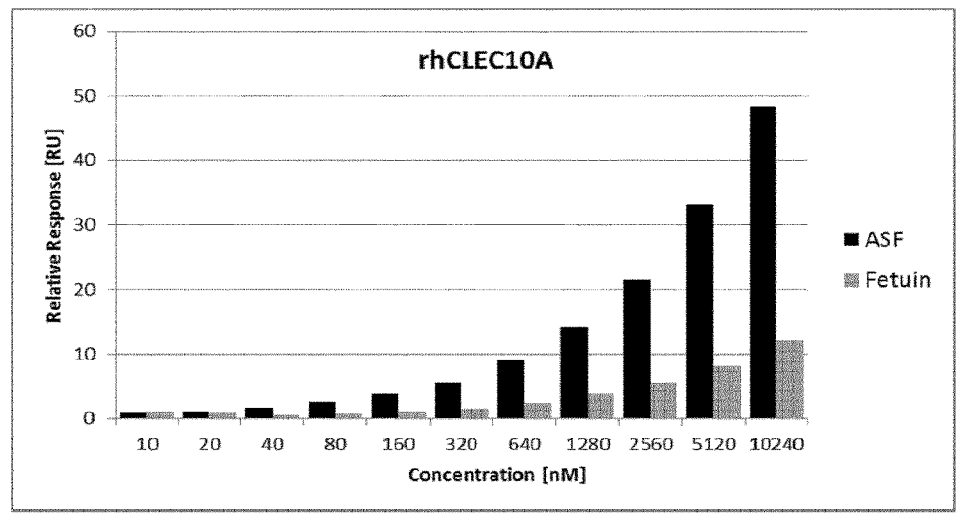

Figure 9, continued:
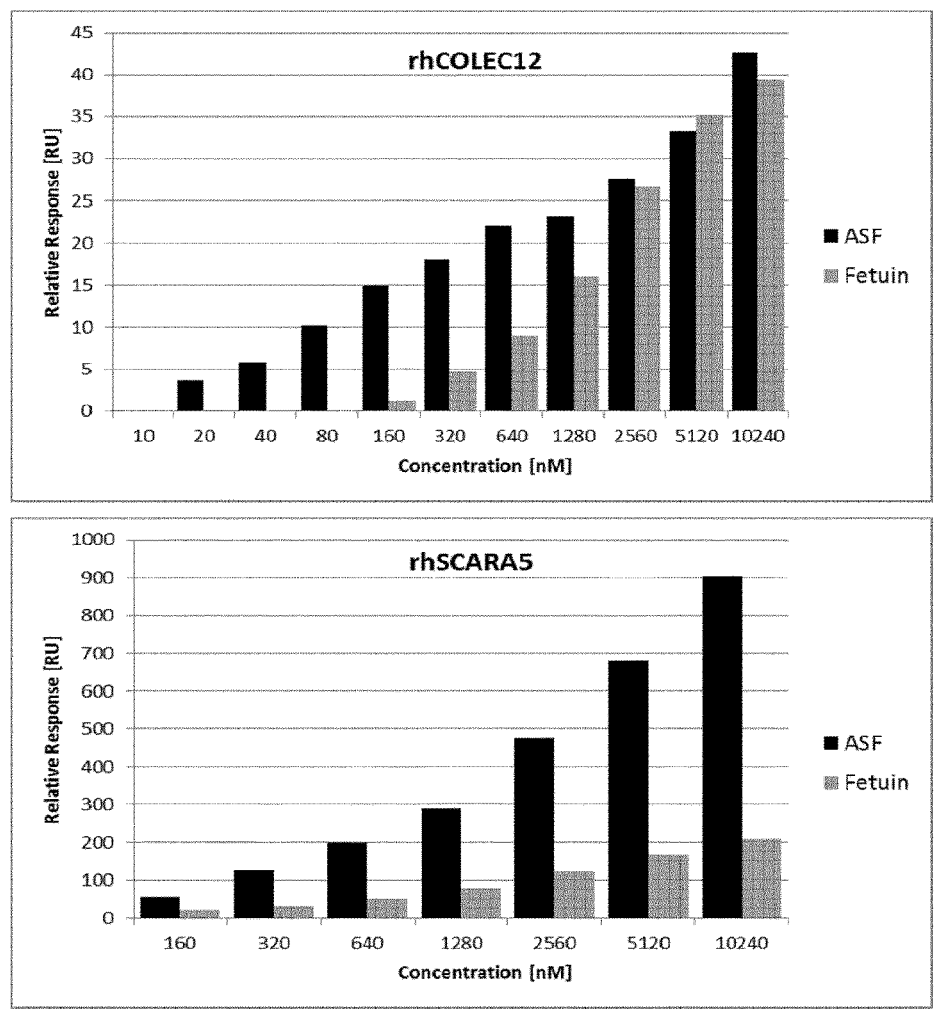

Figure 10, continued:
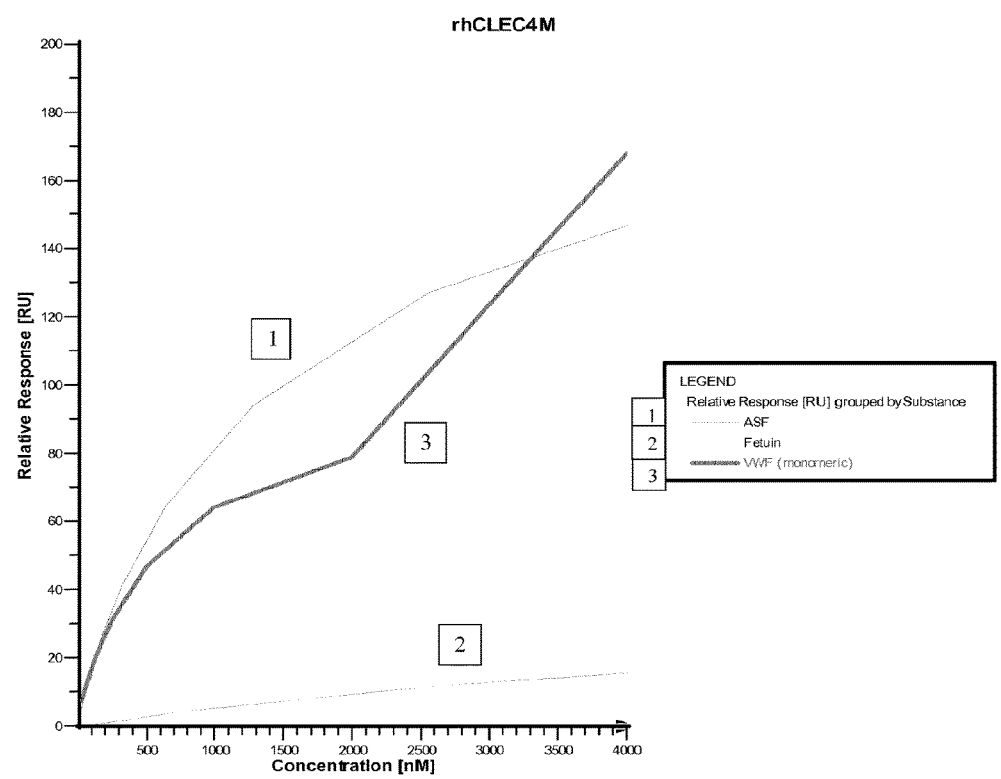

Figure 10, continued:
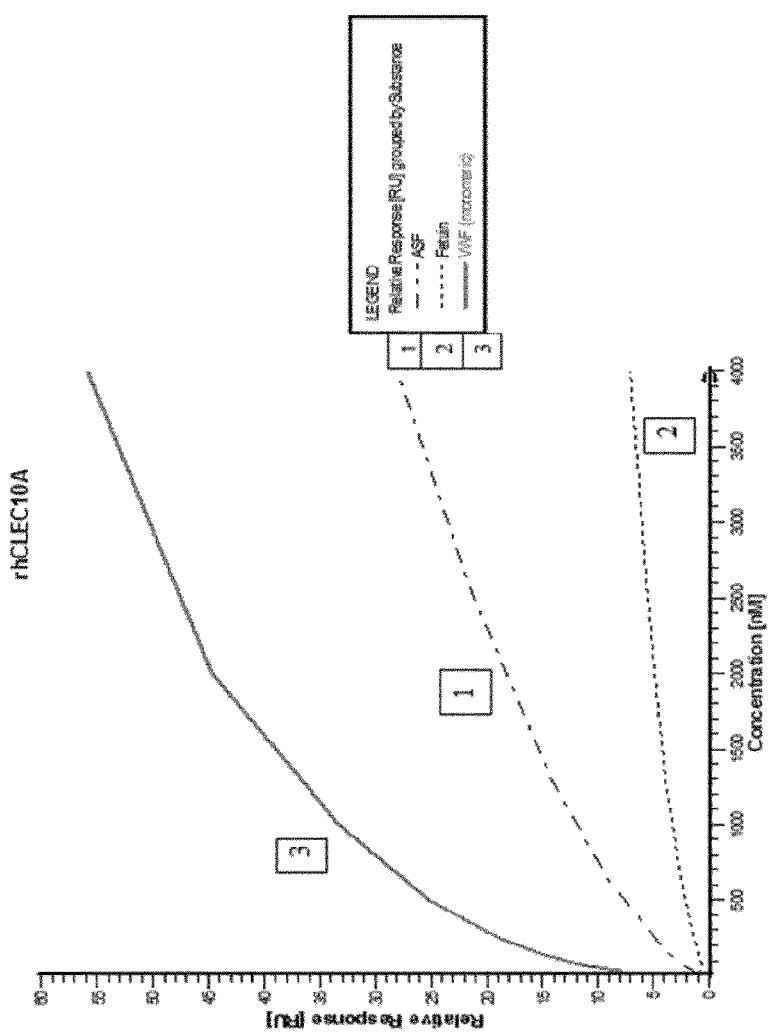

Figure 10, continued:
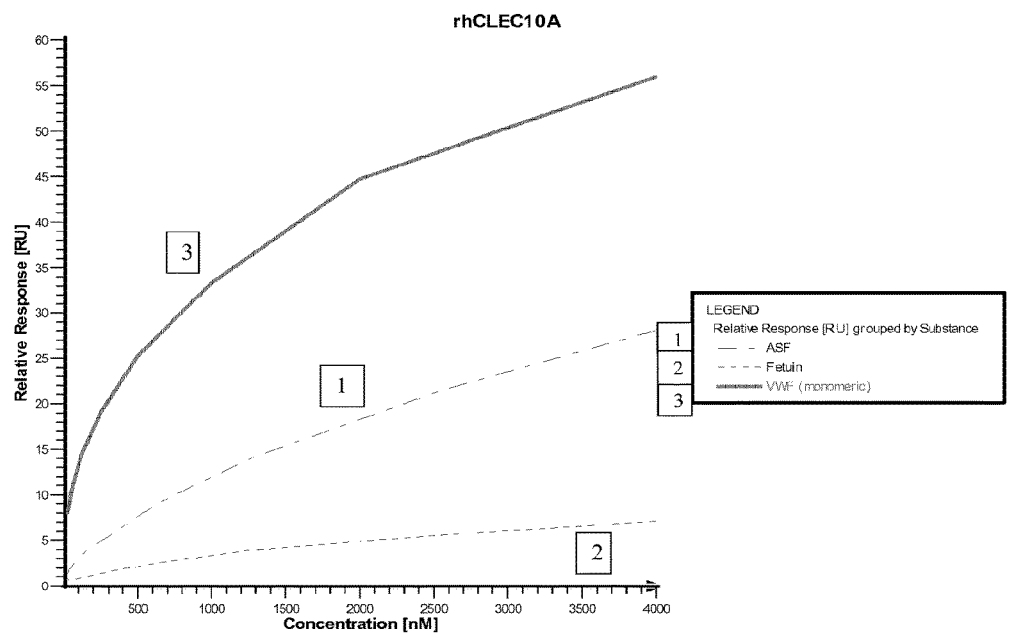

Figure 10, continued:
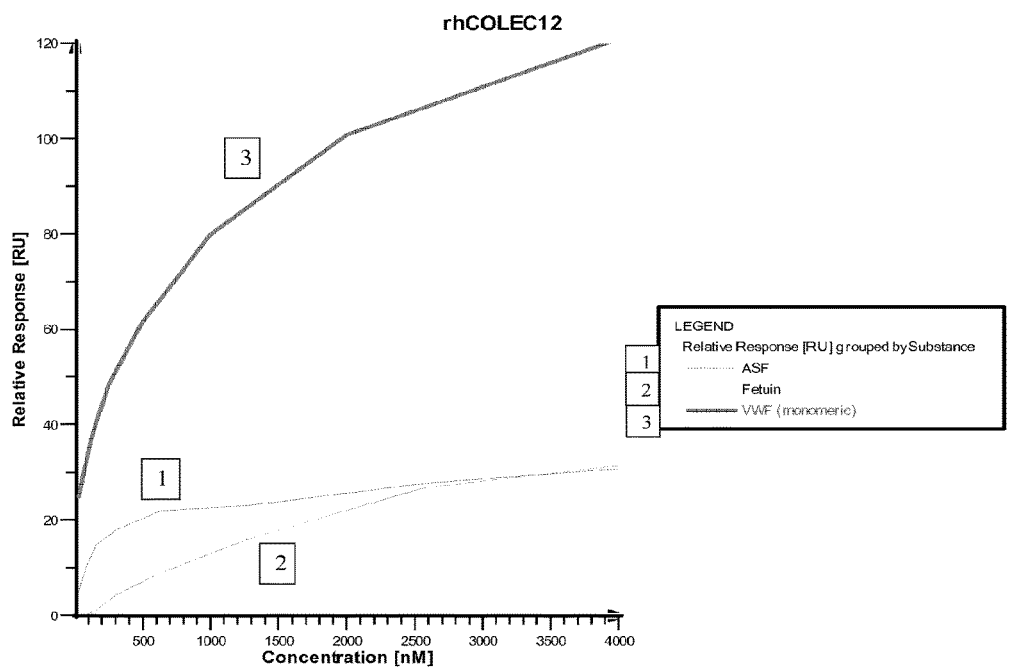

Figure 10, continued:
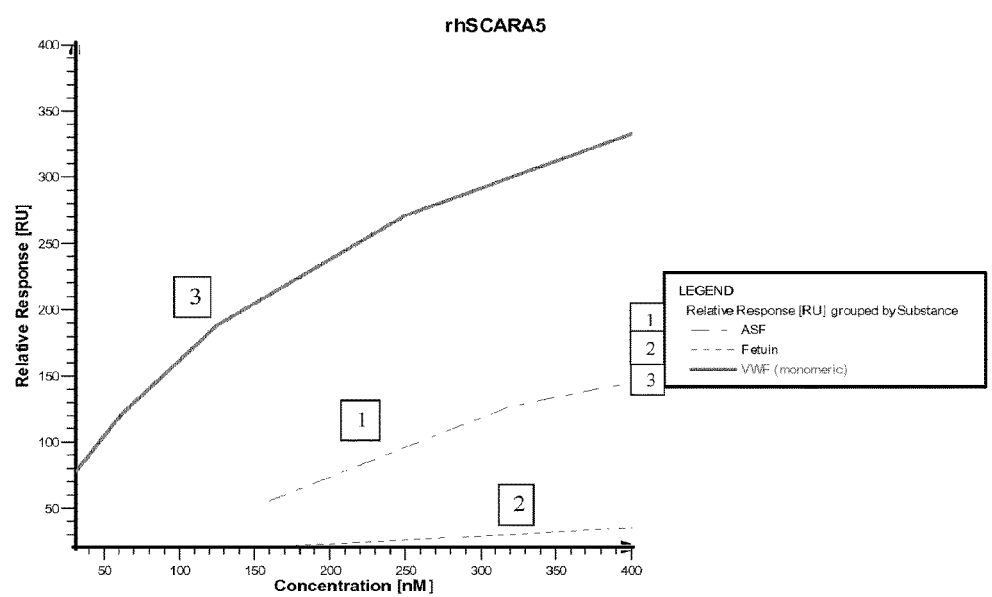

SUGAR COMPOSITIONS FOR TREATING HEMOPHILIA A AND/OR VON WILLEBRAND DISEASE

This is a continuation of application Ser. No. 14/399,326, filed Nov. 6, 2014 which is a National Stage filing of International Application No. PCT/EP2013/055474, filed Mar. 15, 2013, which claims priority of European Patent Application No. 12167178.8, filed May 8, 2012, all of which are incorporated herein by reference.

Von Willebrand factor (VWF) is a large multimeric plasma glycoprotein with two major roles in hemostasis. First, it mediates platelet plug formation at the site of vascular injury through interactions with the subendothelial matrix, followed by platelet activation and aggregation. Second, it acts as carrier molecule for pro-coagulant factor VIII (FVIII). VWF expression is restricted to megakaryocytes and endothelial cells but plasma VWF is mainly derived from endothelium. One of its particular features is a polymer structure ranging in size from 500 kD to more than 20,000 kD, whereby the largest forms are hemostatically the most efficient. During synthesis, VWF undergoes extensive post-translational modification including dimerization, proteolytic cleavage to remove a propeptide and multimerization (De Meyer, Deckmyn, and Vanhoorelbeke, Blood (2009) 113: 5049-57). Along the secretory pathway, to each 2050 amino acid mature monomer 12 N-linked and 10 O-linked glycans are added, accounting for approximately 20% of its total molecular weight (Millar and Brown Blood Rev (2006) 20.2: 83-92). Interestingly, VWF N-glycans as well as O-glycans were shown to carry the ABO(H) blood group antigens (Canis et al. J Thromb Haemost (2010) 8.1: 137-45). Their importance is highlighted by the observation, that individuals of blood group O(H) have 20-30% lower VWF plasma levels than non-O(H) blood groups (Jenkins and O'Donnell Transfusion (2006) 46.10: 1836-44). Although several studies have been performed aimed at investigating the clearance of VWF, the detailed process is not fully understood up to now. Approximately 95% of the plasma FVIII molecules are non-covalently bound to VWF, and it is therefore suggested that VWF-bound FVIII closely follows VWF in its clearance pathway (Lenting, VAN Schooten, and Denis J Thromb Haemost (2007) 5.7: 1353-60).

Deficiency of VWF is responsible for a hemorrhagic disorder called von Willebrand Disease (VWD) whereas elevated plasma levels of VWF represent an important thrombotic risk factor. A variety of plasma-derived concentrates of VWF (with or without FVIII) are available to treat VWD. Current treatment with VWF concentrates often requires repeated, frequent infusions. A reduction in clearance and thereby an extension of the half-life of VWF would reduce the required frequency of infusions and therefore improve the quality of life of VWD patients. In addition, this may also positively impact hemophilia A treatment due to the strong correlation of the FVIII half-life with vWF half-life. (Fijnvandraat, Peters and Ten Cate, British Journal of Haematology (1995): 474-476).

SUMMARY OF THE INVENTION

The inventors have surprisingly found that accessible sugars, preferably the terminal sugars, that are constituents of ABO(H) blood group antigens, have a significant influence on the clearance of VWF. Therefore, one aspect of the invention is a composition comprising an isolated sugar for use in the treatment of VWD and/or hemophilia A, wherein the sugar is an accessible sugar residue derived from ABO(H) blood group antigen. Preferably, the composition leads to a reduction in clearance and increases the in vivo half-life of VWF, more preferably, this leads to a concomitant increase in the FVIII half-life.

The VWF may be endogenously produced, or may be exogenous. It may be plasma-derived or recombinantly produced.

The isolated sugar may be a single sugar or a combination of any two or all of galactose, fucose and N-acetylgalactosamine. The isolated sugar may be part of an oligosaccharide or glycopeptide as an accessible sugar residue, e.g. as a terminal sugar residue, or it may be a monosaccharide, but not the natural ABO(H) blood group antigen on erythrocytes. In addition, chemically modified sugars derived from galactose, fucose and N-acetylgalactosamine may exert the same effect and are therefore also included in the invention.

In case of a subject receiving exogenous VWF, the composition may be administered to a subject in need thereof prior to administration of VWF, or simultaneously with VWF, or even after the administration of VWF. Preferably, the composition of the invention is administered prior to the administration of VWF.

A further aspect of the invention is a pharmaceutical product comprising the composition described above and a composition comprising VWF as a combined preparation for simultaneous, separate or sequential use in the treatment of VWD or hemophilia A.

Another aspect of the invention is a composition comprising VWF and one or more of galactose, fucose or N-acetylgalactosamine or chemically modified forms thereof as a monosaccharide or accessible, e.g. terminal, residue of one or more oligosaccharides or glycopeptides, for use in the treatment of VWD or hemophilia A.

Yet a further aspect of the invention is a composition comprising two or more isolated sugars, wherein the sugar is selected from galactose, fucose and N-acetylgalactosamine or chemically modified forms thereof. The two or more isolated sugars may be present as monosaccharides or as accessible, e.g. terminal sugars of a glycopeptide or oligosaccharide structure but not the natural ABO(H) blood group antigen.

Another aspect of the invention is the composition described above for medical use, in particular for use in the treatment of VWD or hemophilia A.

Preferably, the sugar comprised in any of the compositions detailed above, increases the survival of VWF in the blood of a mammal by inhibiting the interaction of VWF with a clearance receptor.

Preferably, the clearance receptor is a C-type lectin-like receptor, more preferably it is selected from the subgroups of C-type lectin receptors asialoglycoprotein and DC receptors and collectins, according to the definition given in Zalensky & Gready (2005) FEBS-Journal 272, 6179-6217. More preferably, the C-type lectin-like receptor is selected from ASGR, CLEC4M, CLEC10A, CLEC4F, Collectin-12.

In another preferred embodiment, the clearance receptor is a class A scavenger receptor such as scavenger receptor A5 (SCARA5).

DETAILED DESCRIPTION OF THE INVENTION

The inventors have surprisingly found that bovine asialofetuin as well as asialo-alpha-1-acid-glycoprotein, which preferably bind to galactose receptors (e.g. asialoglycoprotein receptor, ASGPR in the liver), block the clearance of VWF, suggesting that such receptors are potential clearance receptors for VWF in vivo. As mentioned above, the inventors have also surprisingly found that the accessible, e.g. the terminal, sugar residues of the ABO(H) blood group antigens by themselves have a significant influence on the clearance of VWF. Therefore, one aspect of the invention is a composition comprising an isolated, unmodified or chemically modified sugar for use in the treatment of hemophilia A and/or VWD, wherein the sugar is, in its natural context, an accessible sugar residue derived from ABO(H) blood group antigen, but is used in an isolated form, i.e. not as part of an ABO(H) blood group antigen.

Preferably, the composition reduces the in vivo clearance of VWF leading to a concomitant increase in the FVIII concentration. Preferably, the in vivo clearance of VWF is reduced at least 1.5 fold, more preferably at least 2 fold, 2.5 fold or 3 fold, even more preferably, the clearance is reduced at least 3.5 fold, 4 fold or 4.5 fold, most preferably the clearance is reduced at least 5 or even 6 fold.

The VWF may be endogenously produced, or may be of exogenous origin. It may be plasma-derived or recombinantly produced. If recombinantly produced, it may be a fusion protein of VWF with a half-life extending moiety, e.g. an albumin fusion or an Fc-fusion. Alternatively, or additionally, the VWF itself may be modified to increase its half-life, e.g. by modifying the glycostructure or by conjugation (e.g. PEGylation, polysialic acids).

The isolated sugar may be one or more of unmodified galactose, preferably D-galactose, more preferably β-D-galactose, fucose, preferably L-fucose, more preferably α-L-fucose, and N-acetylgalactosamine, preferably α-N-acetylgalactosamine and/or chemically modified forms of galactose, fucose and N-acetylgalactosamine that can bind to the clearance receptors, e.g. the ASGPR, with higher affinity. The isolated, possibly chemically modified sugar may be comprised, as an accessible, e.g. terminal, sugar residue, in an oligosaccharide or glycopeptide, but not the natural ABO(H) blood group antigen on erythrocytes, or it may be a monosaccharide. If comprised in an oligosaccharide or glycopeptide, preferably it will be attached to the molecule by the same type of linkage as present in the blood group antigen.

In case of a subject receiving exogenous VWF, the composition may be administered to a subject in need thereof prior to administration of VWF, or simultaneously with VWF, or even after the administration of VWF. Preferably, the composition of the invention is administered prior to the administration of VWF, for example, about 5 minutes prior to the administration of VWF.

A further aspect of the invention is a pharmaceutical product comprising the composition described above and a composition comprising VWF as a combined preparation for simultaneous, separate or sequential use in the treatment of VWD or hemophilia A. The sugar composition may comprise any one or more of unmodified galactose, fucose or N-acetylgalactosamine or chemically modified forms thereof as a monosaccharide or as an accessible, preferably a terminal residue of one or more oligosaccharides or glycopeptides, but not the natural blood group antigen on erythrocytes. Preferably, the sugar composition comprises a mixture of any two, more preferably a mixture of all three of said sugars or chemically modified forms. The VWF may be plasma-derived or recombinant. It may comprise half-life extending moieties. For example, plasma-derived or recombinant VWF may be conjugated with, for example, polyethylene glycol or other physiologically acceptable polymers, conjugated or linked as a fusion protein with albumin, or with an Fc-fragment of IgG. Recombinant VWF may be expressed as a fusion protein with a half-life extending moiety, e.g. as an albumin fusion or an Fc fusion. Recombinant VWF may also be a modified VWF, e.g. comprising amino acid substitutions, deletions or insertions that are introduced in order to modify its properties or to increase its half-life in vivo.

Another aspect of the invention is a composition comprising VWF and one or more of unmodified galactose, fucose or N-acetylgalactosamine or chemically modified forms thereof as a monosaccharide or accessible, e.g. terminal, residue of one or more oligosaccharides or glycopeptides, for use in the treatment of VWD or hemophilia A. The same options as detailed above for the previous aspect of the invention apply here.

Yet a further aspect of the invention is a composition comprising two or more isolated sugars, wherein the sugar is selected from unmodified galactose, fucose and N-acetylgalactosamine or chemically modified forms thereof. The two or more isolated sugars may be present as monosaccharides or as accessible, e.g. terminal, sugars of a glycopeptide or oligosaccharide structure but not the natural ABO(H) blood group antigen.

Another aspect of the invention is the composition described above for medical use, in particular for use in the treatment of VWD or hemophilia A.

Preferably, the sugar comprised in any of the compositions detailed above, increases the survival of VWF in the blood of a mammal by inhibiting the interaction of VWF with a clearance receptor. As already mentioned, the term "sugar" is intended to be interpreted broadly. It may be an unmodified monosaccharide or chemically modified form thereof, or it may be comprised in an oligosaccharide as an accessible, e.g. terminal, sugar; the oligosaccharide may be linear or branched. It may also be a specific carbohydrate structure exposed on a glycopeptide. If it is part of an oligosaccharide or glycopeptide, it is preferably attached through the same type of linkage as in the blood group antigen.

Preferably, the clearance receptor is a C-type lectin-like receptor, which is a class of animal (and human) lectins that bind to a carbohydrate in a calcium-dependent manner. More preferably, the clearance receptor is selected from the following subgroups of C-type lectin receptors: asialoglycoprotein and DC receptors and collectins. More preferably, the C-type lectin-like receptor is selected from ASGPR, CLEC4M, CLEC10A, CLEC4F, Collectin-12.

In another preferred embodiment, the clearance receptor is a class A scavenger receptor such as scavenger receptor A5 (SCARA5).

C-type lectin-like receptors are reviewed in Zalensky & Gready (2005) FEBS-Journal 272, 6179-6217, incorporated herein by reference in its entirety. Asialoglycoprotein and DC receptors are a subgroup of C-type lectin-like receptors. They are type II transmembrane proteins containing a short cytoplasmic tail, a transmembrane domain, an extracellular stalk region and a $Ca^{2+}$/carbohydrate binding C-type lectin domain. The length of the stalk region, which is involved in oligomerization, varies greatly among different members of this subgroup. Members of this subgroup are, for example, asialoglycoprotein receptor, macrophage galactose-binding lectin (MGL), dendritic cell-specific intercellular adhesion molecule-3-grabbing non-integrin (DC-SIGN), and others. Asialoglycoprotein receptor is a heterotrimer, expressed on liver parenchyma, encoded by two genes (ASGR1 and ASGR2). It binds and internalizes galactose-terminated oligosaccharides of desialylated glycoproteins. After ligand dissociation in acidic lysosomes, it is recycled to the cell surface.

Collectins are a different subgroup of C-type lectin-like receptors. They contain a collagen domain and function as part of the first in line innate immune defense.

CLEC4M, CLEC10A, and CLEC4F are also C-type lectin domain family members.

SCARA-5 belongs to a group of scavenger molecules that have as their primary function the initiation of immune responses. It is expressed on epithelial cells.

The dose of the isolated sugar can be in the range of 30 mg to 10 g per kg, preferably 50 mg to 8 g per kg, more preferably 100 mg to 6 g per kg of the monosaccharide or molar equivalents thereof if the sugar is comprised in an oligosaccharide or glycopeptide, preferably 200 mg to 4 g per kg, more preferably 250 mg to 3 g per kg. The skilled person will be able to determine the optimal dose as a matter of routine.

The term "isolated sugar" is meant to refer to the respective sugar when not part of the natural ABO(H) blood group antigen. It may be an unmodified monosaccharide or chemically modified form thereof, or as an accessible, e.g. terminal, sugar comprised in an oligosaccharide, which may be linear or branched. It may also be a specific carbohydrate structure exposed on glycopeptides. If it is part of an oligosaccharide or glycopeptide, it is preferably attached through the same type of linkage as in the blood group antigen.

The term "oligosaccharide" refers to a chain of sugar residues with 2 or more residues, preferably 3 or more residues.

The term "glycopeptides" refers to a peptide or protein with one or more glycan structures attached, e.g. O-linked or N-linked. The glycan structure may be linear or branched, and it may comprise one or more sugar residues.

The term "half-life" refers to the time it takes to eliminate half of the protein from the circulation in vivo. The area under the curve (AUC) was predominantly determined to assess clearance effects. A reduction in clearance leads to higher AUC values, and to an increase in half-life.

The term "ABO(H) blood group antigen" refers to carbohydrate antigens present on erythrocytes that are commonly recognized by anti-A or anti-B antibodies. The ABO (H) blood group system is the most important blood type system in human blood transfusion. The H-antigen is an essential precursor to the ABO(H) blood group antigens, and is a carbohydrate structure linked mainly to protein, with a minor fraction attached to ceramide. It consists of a chain of β-D-galactose, β-D-N-acetylglucosamine, β-D-galactose, and 2-linked α-L-fucose. The A-antigen contains an α-N-acetylgalactosamine bonded to the D-galactose residue at the end of the H-antigen, whereas the B-antigen has an α-D-galactose residue bonded to the D-galactose of the H-antigen. Therefore, the terminal sugar residues of the ABO(H) blood group system are galactose, N-acetylgalactosamine and fucose.

The term "von Willebrand factor" (VWF) refers to a blood glycoprotein involved in hemostasis. It promotes adhesion of platelets to the sites of vascular injury by forming a molecular bridge between the sub-endothelial collagen matrix and platelets. It is also a carrier for coagulation FVIII, protecting it from degradation and clearance. The term may relate to the natural VWF, but also includes variants thereof, e.g. fusion proteins or conjugates, or sequence variants where one or more residues have been inserted, deleted or substituted, maintaining at least one biological function.

The term "hemophilia A" refers to a deficiency in coagulation FVIII, which is usually inherited.

The term "von Willebrand disease" (VWD) refers to a coagulation abnormality associated with a qualitative or quantitative deficiency of VWF.

The term "accessible sugar residue" refers to a sugar residue that is exposed on the surface of a glycoprotein or oligosaccharide, in particular the term refers to a sugar residue that is capable of binding to endothelial or other structures to which vWF binds and which thereby competitively blocks the binding of vWF to these receptors.

The term "clearance receptor" in the context of the present invention refers to any molecule that binds VWF and leads to the elimination of the bound molecule from the blood stream. Typically the clearance will be by receptor-mediated endocytosis, and the bound molecule will be degraded in the lysosomal compartment.

EXAMPLES

The invention is exemplified by the following, non-limiting examples, with reference to the following figures.

EXAMPLE 1: INFLUENCE OF MONOSACCHARIDES ON THE CLEARANCE OF HUMAN PLASMA-DERIVED VWF IN RATS AND MICE

Blood group sugars A, B and O(H) consist of three different monosaccharide units (for H only two); namely galactose (Gal), fucose (Fuc) and N-acteylgalactosamine (GalNAc). To evaluate the effect of these sugars on the clearance of pd-VWF, rats were injected i.v. with a bolus of a "sugar-mix", consisting of Gal, Fuc and GalNAc, obtained from Sigma Aldrich, St Louis, USA, (each 2 g/kg) 15 minutes before infusion of Haemate® P (200 IU/kg) type O(H). Alternatively, each sugar was used individually at 2 g/kg. To avoid masking of the blood group antigens present on VWF by blood group-specific antibodies, material isolated from blood group type O(H) individuals was used. In addition, bovine asialofetuin (250 mg/kg), a described ligand for blocking the galactose receptors such as the ASGPR in the liver has been additionally used. Furthermore, glucose (2 g/kg) was included in the study as a negative control. Blood samples were collected and analyzed for human VWF antigen by ELISA.

Figure 1:
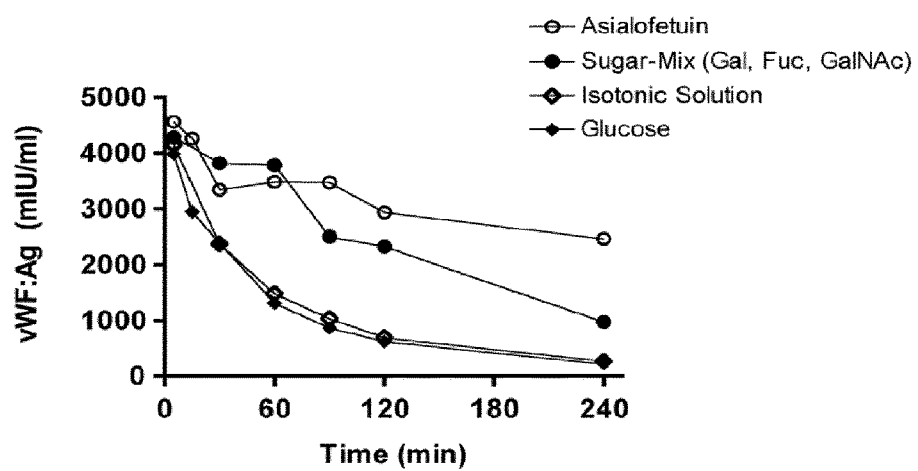
FIG. 1 shows the reduction in clearance (increase in AUC) of VWF by a mix of 3 sugars in rats.
Figure 2:
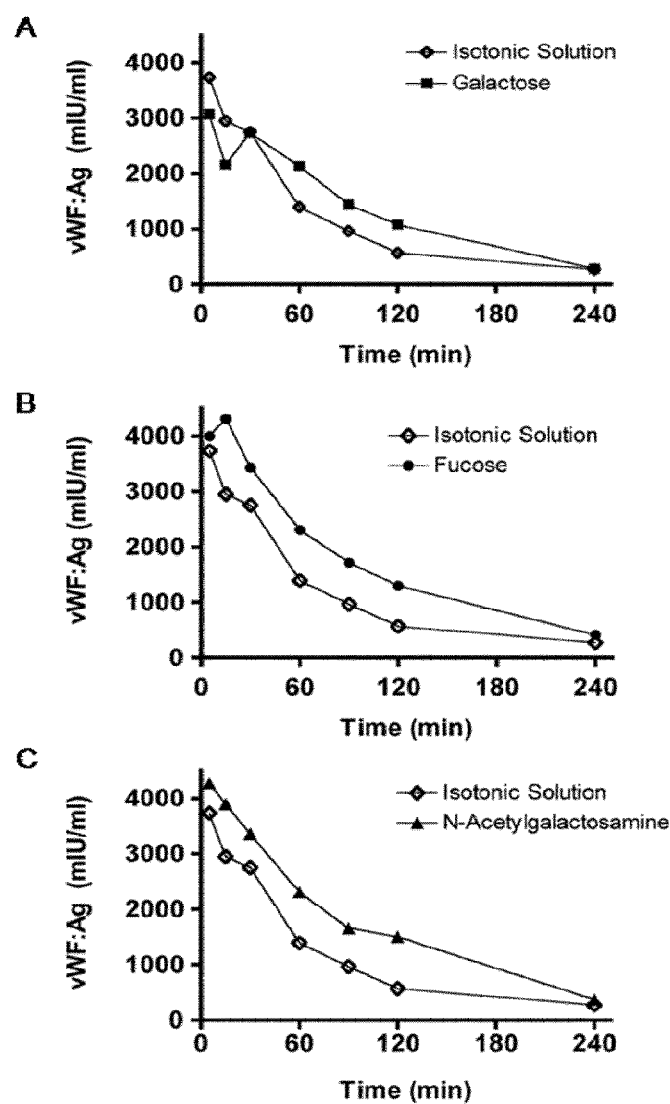
FIG. 2 shows the effect of each individual sugar on the clearance of VWF in rats.

As shown in FIG. 1, the solution containing Gal, Fuc and GalNAc markedly increased AUC and thereby delayed the clearance of VWF. The effect of each individual sugar is shown in FIG. 2. Interestingly, Gal alone had only a modest effect on VWF clearance, whereas Fuc and GalNac had a more pronounced effect on inhibiting the clearance of VWF.

EXAMPLE 2: EFFECT OF FUC, GAL AND GALNAC ON THE CLEARANCE OF PLASMA DERIVED VWF IN VWF-DEFICIENT MICE

Figure 3:
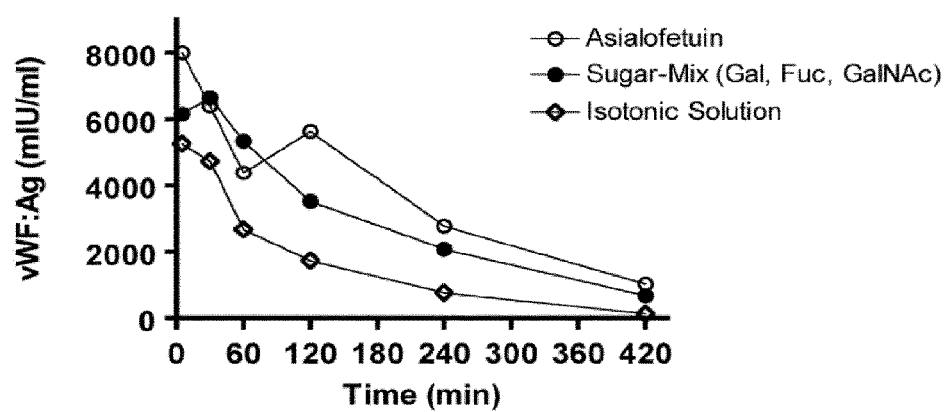
FIG. 3 shows the effect of a mix of 3 sugars on the clearance of VWF in VWF-deficient mice.

The effect of the sugars on the clearance of human plasma-derived (pd) VWF was also evaluated in VWF-deficient mice. The animals received a bolus of a "sugar-mix" i.v., consisting of Gal, Fuc and GalNAc (each 2 g/kg) 15 minutes before infusion of Haemate® P (200 IU/kg) type O(H). As shown in FIG. 3, a comparable effect as shown before in rats of the sugar-mix on clearance of pd-VWF was observed in VWF-deficient mice.

EXAMPLE 3: EFFECT OF SUGAR DOSE

Specific sugar doses related to each of the approaches described above are evaluated in animal research models such as rats and/or VWF-deficient mice aiming to find the appropriate concentration for in vivo application. Different sugar concentrations are administered intravenously. For example, a range of sugar concentrations from 30 mg/kg to about 6 g/kg can be used, and the sugars are used individually and in combinations of two or all three sugars. Oral administration of the different sugar concentrations is also part of the investigation. Concomitantly to the sugar administration described, plasma derived or recombinant VWF or preparations containing both VWF and FVIII are co-administered; alternatively, the administration of VWF or VWF and FVIII is delayed by about 5 minutes following administration of the sugar(s). After administration, VWF antigen levels are continuously monitored by applying a standardized ELISA system. In case of FVIII administration, FVIII antigen levels are measured in addition. Different sugar doses reveal a significant increase in AUC, resulting in a reduction of the VWF (and FVIII) clearance. The respective approaches are further investigated within in-vivo toxicology studies with regard to compatibility.

EXAMPLE 4: EFFECT OF OLIGOSACCHARIDES

As described in examples 1 to 3, equivalent experimental approaches are applied for evaluating the clearance reduction of both VWF and FVIII due to the administration of oligosaccharides. For example, trisaccharides corresponding to the blood group antigens are used, alone and in combination. For the initial evaluation, a dose of about 2 g per kg may be chosen; a dose finding study as described in example 3 for monosaccharides is also carried out.

The clearance of VWF (and FVIII) is markedly reduced in the presence of specific oligosaccharides.

EXAMPLE 5: EFFECT OF GLYCOPEPTIDES

The effect of asialo-glycopeptides on both the clearance of human pd VWF as well as recombinant FVIII was evaluated in VWF-deficient mice. The animals received a bolus of either asialo-alpha-1-acid-glycoprotein (asialo-AGP) or asialo-fetuin 5 minutes before infusion of highly purified pd VWF (plasmatic FVIII was removed) previously mixed with recombinant FVIII. VWF and recombinant FVIII were administered in a concentration of 200 IU/kg. The pd VWF is biochemically comparable (glycosylation, multimer distribution, etc.) to Haemate® P.

Figure 4:
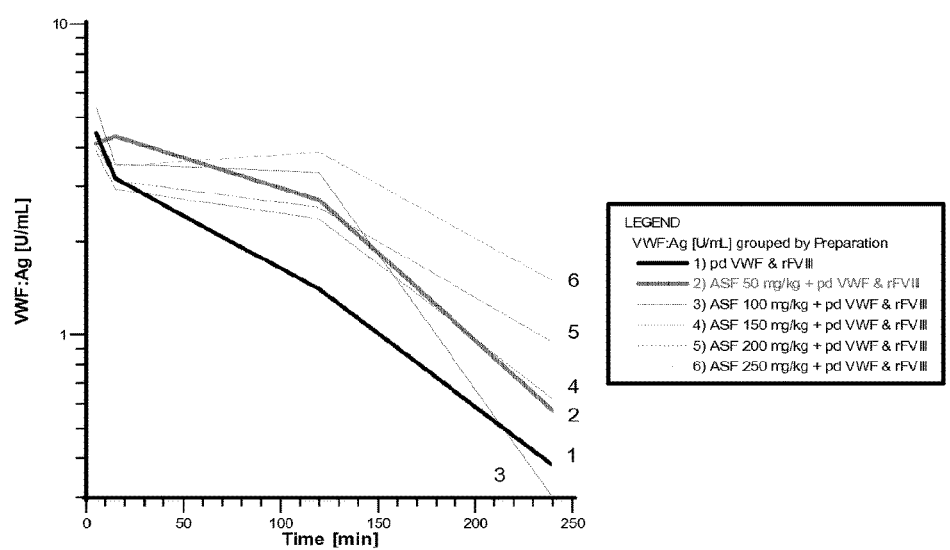
FIG. 4 shows the reduction in clearance of pdVWF in VWF-deficient mice by different doses of asialofetuin.
Figure 5:
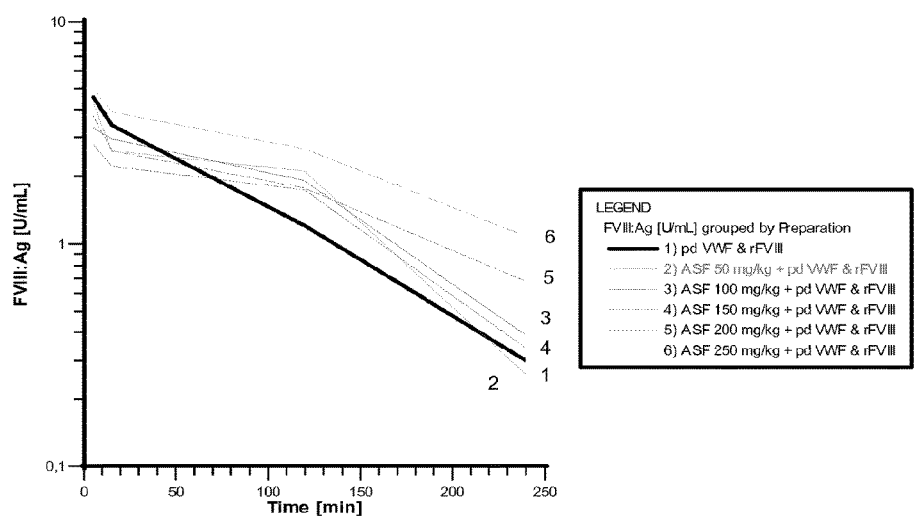
FIG. 5 shows the reduction in clearance of rFVIII in VWF-deficient mice by different doses of asialofetuin.
Figure 6:
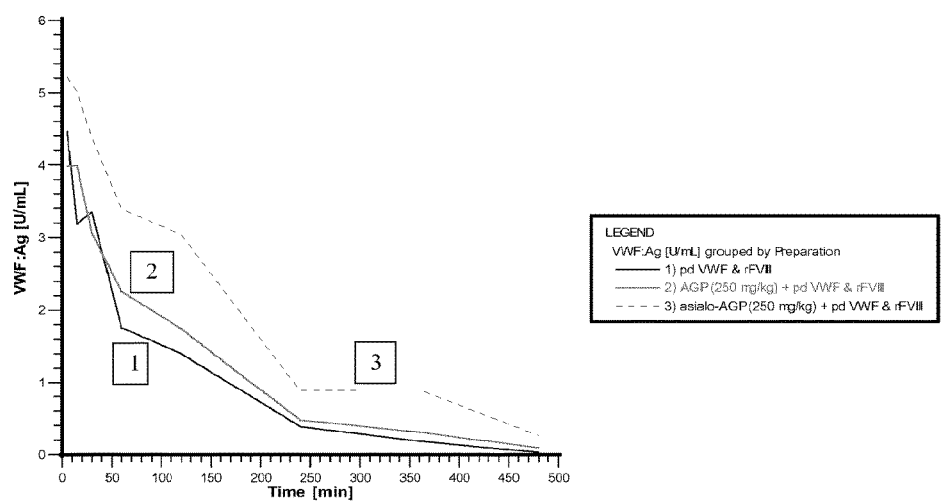
FIG. 6 shows the reduction in clearance of VWF in VWF-deficient mice by asialoAGP.

As shown in FIG. 4, a reduced clearance was observed for pd VWF in the presence of an asialofetuin concentration of equal or more than 100 mg/kg (dashed lines). In addition, the reduction in clearance of VWF affects also the clearance process of FVIII as demonstrated in FIG. 5. A reduction in VWF clearance caused by asialofetuin also leads to a reduction in FVIII clearance. The same effect was observed by applying asialo-AGP (bolus of 250 mg/kg). An overview of the respective test results is given in FIG. 6. Moreover, fetuin and alpha-1-acid-glycoprotein (AGP) were used as control substances. These materials bear terminal sialic acid instead of terminal galactose residues characteristic for the asialo-preparations. As expected, the control substances did not show a significant effect regarding reduction in clearance.

Figure 7:
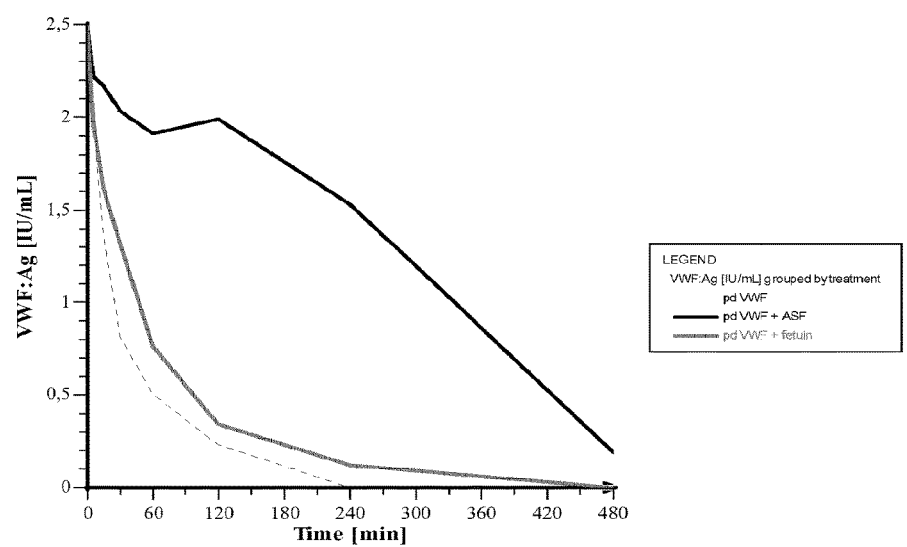
FIG. 7 shows the prolonging effect of ASF on the clearance of VWF in rats in comparison to the control group with fetuin.

In addition, as shown in FIG. 7, it was clearly shown that the clearance of VWF is reduced in the presence of bovine ASF (fetuin after the removal of terminal sialic acid residues) whereas the effect of bovine fetuin on the clearance of VWF is less significant.

Figure 8:
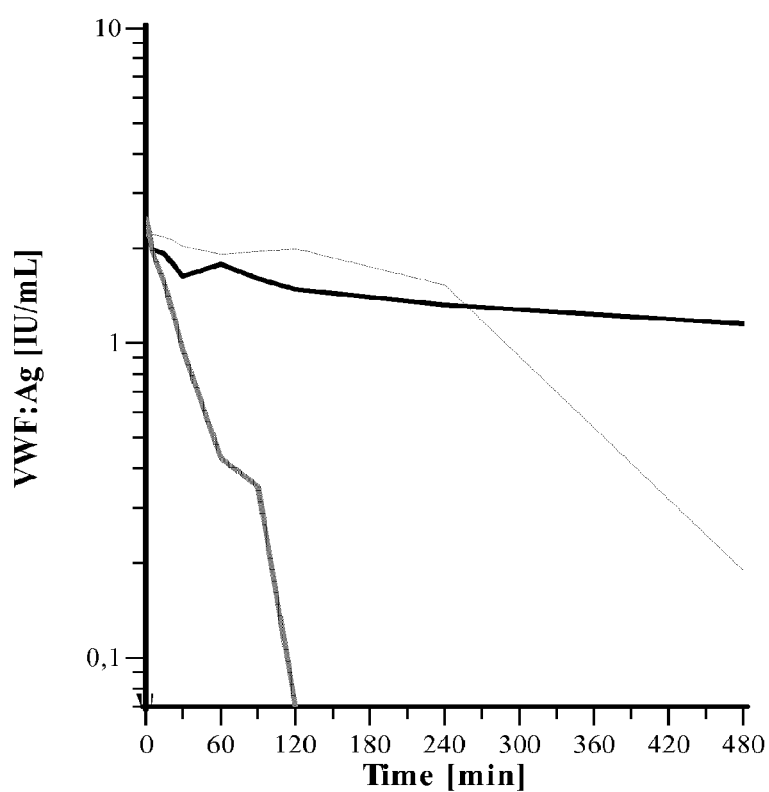
FIG. 8 shows that clearance of VWF was inhibited by administering multiple doses of ASF.

Furthermore, the prolonging effect of ASF on VWF clearance was maintained by administering ASF frequently (intravenous administration of ASF in rats at 5 min, 120 min, 240 min and 360 min after the intravenous administration of 100 IU VWF per kg body weight), as shown in FIG. 8. These data are compared with the clearance of VWF in the presence of ASF that was administered as single dose as well as a multi dose administration of isotonic NaCl solution used as control group.

EXAMPLE 6: INTERACTION WITH POTENTIAL CLEARANCE RECEPTOR CANDIDATES

Due to the fact that asialo-glycoproteins as well as monosaccharides have interestingly led to a prolonged half-life of VWF (and FVIII) in vivo, respective cellular receptors were investigated with regard to interacting with VWF. These studies were performed in vitro and potential clearance receptor candidates were identified that might play a crucial role in VWF clearance due to interacting with both ASF and VWF.

Method

SPR technology (Biacore T200, GE Healthcare Biosciences, Uppsala, Sweden) was applied to evaluate mechanisms of realtime biomolecular interactions between VWF, receptor-blocking agents and clearance receptor candidates. The interaction experiments were performed at a flow cell temperature of +25° C. by applying running buffer containing 10 mM HEPES, 150 mM NaCl, 5 mM CaCl2 and 0.05%

Tween-20 at pH 7.4, which was also used as sample dilution buffer. Reagents and buffer stock solutions were purchased from GE Healthcare Biosciences (Uppsala, Sweden). The extracellular domains of receptor proteins were acquired from R&D Systems (Wiesbaden, Germany). The ligands were captured on Series S Sensor Chips C1 pretreated according to the manufacturer's instructions. The receptor proteins were covalently immobilized through free amine groups to the carboxymethylated dextran matrix by applying the amine coupling kit according to the manufacturer protocol. A blank flow cell without immobilized protein was included as a reference surface on the chip for bulk shift and nonspecific binding changes.

Increasing concentrations of both ASF and fetuin ranging from 10,240 to 10 nM were prepared as a 2 fold serial dilution series in running buffer and sequentially injected across the chip surface at 25 µL/min in order to characterize protein-ligand interaction. For the experiments performed with purified VWF monomers (pd VWF after reduction with dithiothreitol and carboxymethylation with iodoacetamide), the concentrations ranged between 4,000 and 31.25 nM. The samples were designed to contain similar buffer compositions due to the high sensitivity of the SPR system to changes in buffer composition. The relatively high flow rate was chosen to avoid potential rebinding due to mass transfer limitations. Interaction analysis cycles consisted of a 5 min sample injection phase. This association phase was followed by a dissociation phase of 17 min in running buffer. Both the chip surface and the control surface were regenerated with a 10 second pulse of 10 mM NaOH between each run in order to remove bound analyte from the surface-immobilized receptor proteins.

Kinetic data were analyzed using Biacore T200 Evaluation Software Version 1.0 (GE Healthcare Biosciences, Uppsala, Sweden). An interaction of the analyte with the ligand was detected by an increase in accumulating mass and specific binding was identified by subtracting the binding response recorded from the control surface, followed by subtracting an average of the buffer blank injections. A report point was positioned 20 seconds after the end of sample injection and was evaluated as representative for a stable protein-ligand interaction, which was of interest. Thus, this point was used for the assessment and calculation of the biomolecular interactions between the analytes and potential clearance receptor candidates. Furthermore, the response was calculated relative to the baseline in each case.

Figure 9:
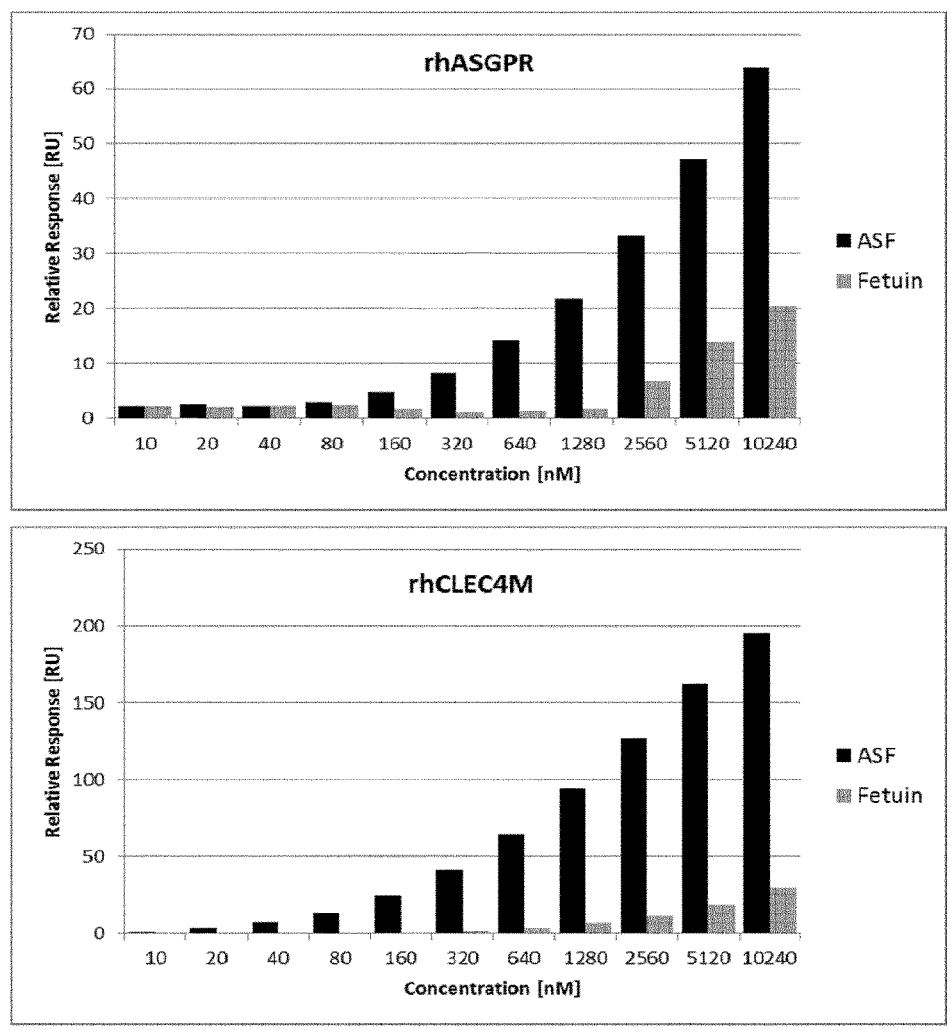
FIG. 9 shows increased binding signals of ASF to immobilized clearance receptor proteins in comparison to fetuin used as control protein.
Figure 10:
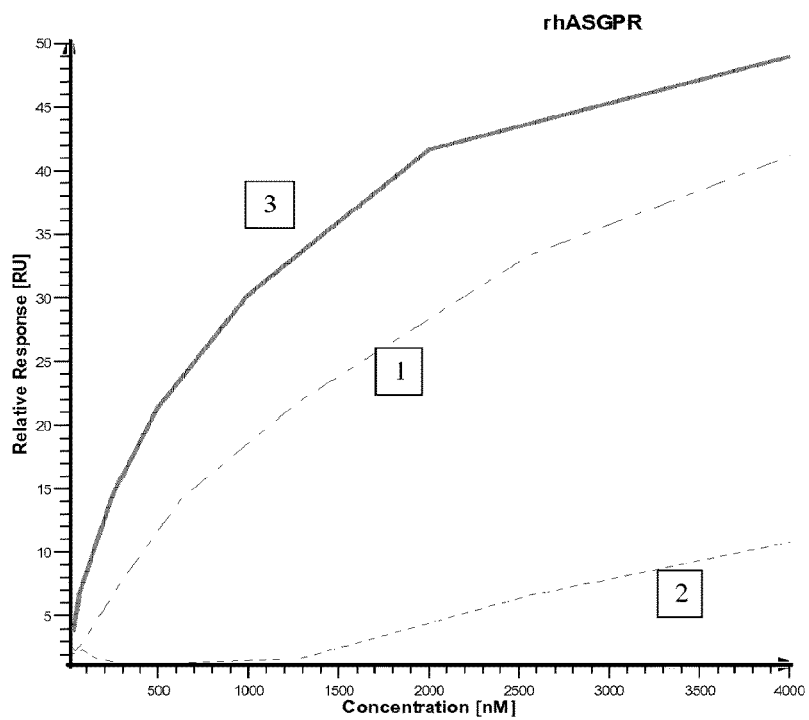
FIG. 10 shows relative SPR binding signals of different concentrations of VWF monomers in comparison to ASF and fetuin by applying different clearance receptor proteins covalently immobilized on a chip.
Figure 10:

An overview of the binding results and the involved clearance receptor candidates interacting with VWF and ASF (and almost not with fetuin) are shown in FIGS. 9 and 10. In conclusion, VWF and ASF bind efficiently to rhASGPR, rhCLEC4M, rmCLEC4F, rhCLEC10A, rhCOLEC12 and rhSCARA5. Thus, these receptor candidates are suggested to play a crucial role in VWF clearance.

EXAMPLE 7: INHIBITION OF ASF INTERACTING WITH RHASGPR BY USING DIFFERENT MONOSACCHARIDES

Figure 11:
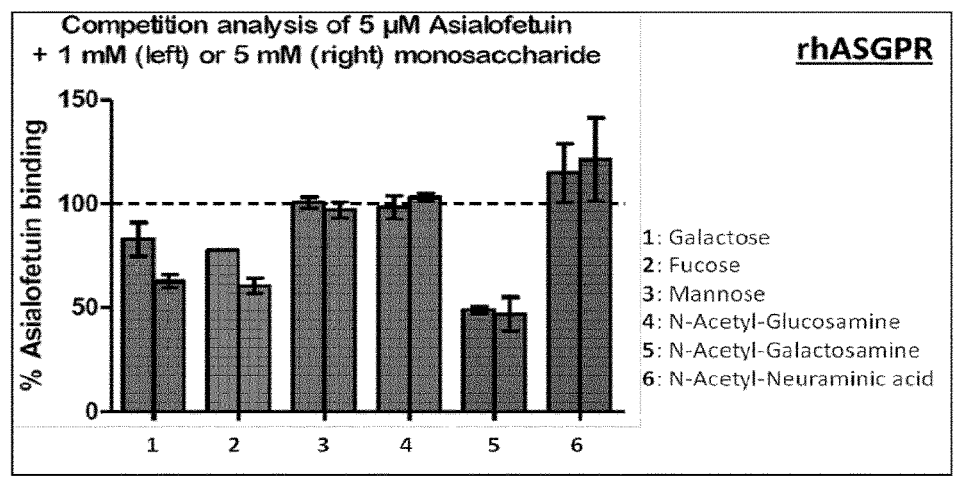
FIG. 11 shows decreased binding of ASF to immobilized rhASGPR in the presence of galactose, fucose and N-acetylgalactosamine.

RhASGPR was chosen for further experiments. A similar SPR approach was used in order to investigate the inhibition of ASF binding in the presence of monosaccharides. Interestingly, galactose, fucose and N-acetylgalactosamine inhibited binding, a phenomenon that is in agreement with the observations from animal studies performed previously (see FIG. 11). In addition, binding of ASF was inhibited in the absence of Ca2+.

EXAMPLE 8

According to example 7, the interaction of pd VWF monomers with clearance receptors mentioned earlier is inhibited in the in the presence of monosaccharides such as galactose, fucose and N-acetylgalactosamine.

EXAMPLE 9: SOLID-PHASE BINDING ASSAY FOR INVESTIGATING RECEPTOR-LIGAND INTERACTION

In addition to SPR-based interaction analysis with monomeric VWF, the interaction of multimeric VWF (purified from human plasma) with rhASGPR was investigated by using solid-phase binding assay. In addition, asialo-VWF (plasma derived VWF after treatment with α(2-3,6,8)-neuraminidase) was used as control.

Lyophilized rhASGPR (R&D Systems, Wiesbaden, Germany) was reconstituted and diluted in 0.05 M carbonate-bicarbonate buffer at pH 9.6, adsorbed onto high-adsorption 96-microwell plates at RT overnight, and subsequently washed with washing buffer (50 mM Tris, 150 mM NaCl, 5 mM CaCl2 and 0.1% (w/v) Tween-20 at pH 7.4). Afterwards, the wells were incubated for 1 hour with blocking solution (50 mM Tris, 150 mM NaCl, 5 mM CaCl2 and 2.5% (w/v) BSA at pH 7.4) in order to block non-specific binding, and then washed with washing buffer again. Samples were diluted with dilution buffer (50 mM Tris, 150 mM NaCl, 5 mM CaCl2, 0.1% (w/v) Tween-20 and 1% (w/v) BSA at pH 7.4) to VWF concentrations ranging from 100 to 3 µg/mL. VWF interacted with the immobilized receptor protein while incubating the samples for 1 hour at +37° C. After washing the wells, associated VWF was subsequently detected by a commercial polyclonal rabbit anti-human VWF antibody conjugated with HRP (DakoCytomation, Glostrup, Denmark) that had been previously diluted 1:16,000 in dilution buffer. The wells were incubated with the HRP-conjugated antibody solution for 1.5 hours at RT and washed before the substrate solution, a chromogenic TMB substrate diluted 1:11 in TMB substrate buffer (Siemens Healthcare Diagnostics, Marburg, Germany), was added and incubated for 30 minutes at RT in the dark. All washing steps were performed for three times. The reaction was stopped with stopping solution POD (Siemens Healthcare Diagnostics, Marburg, Germany) and the substrate reaction was photometrically monitored by measuring the difference in wave lengths at 450 nm and 620 nm.

Figure 12:
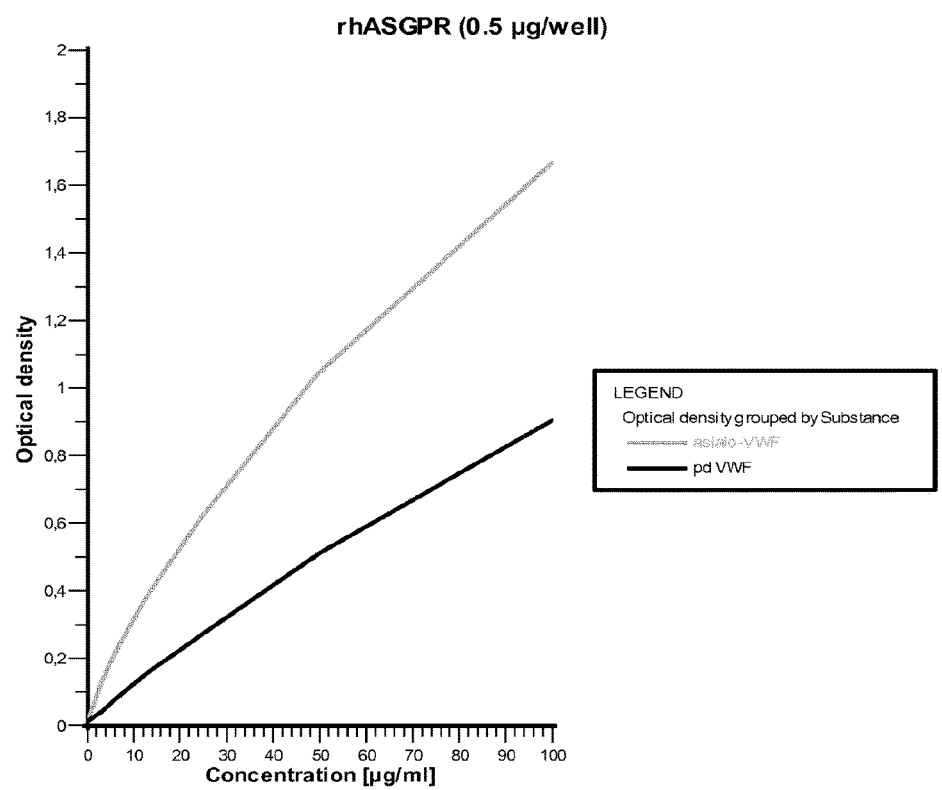
FIG. 12 shows the binding of plasma derived VWF multimers to rhASGPR by applying a solid-phase binding assay.

The results are given in FIG. 12. Not only asialo-VWF multimers interacted with rhASGPR but also plasma derived VWF multimers presenting a native glycosylation structure without modifications.

EXAMPLE 10

According to Example 9, pd VWF multimers interact with clearance receptor candidates mentioned earlier. In addition, binding is inhibited in the presence of ASF or monosaccharides such as galactose, fucose and N-acetylgalactosamine.

The invention claimed is:
1. A method of increasing the half-life of von Willebrand factor in the blood of a subject with hemophilia A and/or von Willebrand disease, comprising administering to the subject a composition comprising an isolated sugar that inhibits the interaction of von Willebrand factor with its clearance receptor, wherein the sugar is a glycopeptide comprising an accessible sugar residue derived from ABO(H) blood group antigen, and wherein the accessible sugar residue is attached to the glycopeptide by the same type of linkage as present in the blood group antigen.

2. The method of claim 1, wherein the in vivo clearance of von Willebrand factor is reduced.

3. The method of claim 2, wherein the reduction of in vivo clearance of von Willebrand factor leads to a concomitant increase in the area under the curve representing factor VIII concentration.

4. The method of claim 2, wherein the von Willebrand factor is endogenously produced.

5. The method of claim 1, wherein the method further comprises administering exogenous von Willebrand factor.

6. The method of claim 5, wherein the exogenous von Willebrand factor is plasma-derived.

7. The method of claim 5, wherein the exogenous von Willebrand factor is recombinant.

8. The method of claim 5, wherein the composition is administered to a subject prior to administration of exogenous von Willebrand factor.

9. The method of claim 1, wherein the sugar is an asialo-glycopeptide, or chemically modified derivative thereof.

10. The method of claim 1, wherein the clearance receptor is a C-type lectin-like receptor.

11. The method of claim 10, wherein the C-type lectin-like receptor is selected from the subgroups asialoglycoprotein, DC receptors, and collectins.

12. The method of claim 10, wherein the C-type lectin-like receptor is selected from ASGPR, CLEC4M, CLEC10A, CLEC4F, and Collectin-12.

13. The method of claim 1, wherein the clearance receptor is a class A scavenger receptor comprising scavenger receptor A5 (SCARA5).

14. A method of increasing the half-life of von Willebrand factor in the blood of a subject with hemophilia A and/or von Willebrand disease, comprising administering to the subject a composition comprising von Willebrand factor and an isolated sugar that inhibits the interaction of von Willebrand factor with its clearance receptor, wherein the sugar is a glycopeptide comprising an accessible sugar residue derived from ABO(H) blood group antigen, and wherein the accessible sugar residue is attached to the glycopeptide by the same type of linkage as present in the blood group antigen.

15. The method of claim 14, wherein the in vivo clearance of von Willebrand factor is reduced.

16. The method of claim 15, wherein the reduction of in vivo clearance of von Willebrand factor leads to a concomitant increase in the area under the curve representing factor VIII concentration.

17. The method of claim 14, wherein the administered von Willebrand factor is recombinant.

18. The method of claim 14, wherein the sugar is an asialo-glycopeptide, or chemically modified derivative thereof.

19. The method of claim 14, wherein the clearance receptor is a C-type lectin-like receptor.

20. The method of claim 14, wherein the clearance receptor is a class A scavenger receptor comprising scavenger receptor A5 (SCARA5).

* * * * *